United States Patent [19]

Moss et al.

[11] Patent Number: 5,483,164

[45] Date of Patent: Jan. 9, 1996

[54] WATER QUALITY SENSOR APPARATUS

[75] Inventors: Adrian J. Moss, Aldershot; John Hewinson; Peter Walton, both of Poole; Brian J. Birch, Chelveston; Clare L. Ball, Rushden; Andrew W. James, West End; John K. Atkinson, Romsey; Przemyslaw R. Siuda, Southampton, all of, England

[73] Assignee: Siemens Plessey Controls Limited, Dorset, England

[21] Appl. No.: 314,495

[22] Filed: Sep. 28, 1994

[30] Foreign Application Priority Data

Nov. 2, 1993 [GB] United Kingdom ............. 9322563
Dec. 1, 1993 [GB] United Kingdom ............. 9324663

[51] Int. Cl.[6] .................... G01N 27/00; G01N 27/27
[52] U.S. Cl. .................. 324/425; 324/438; 324/439; 324/693; 204/406; 204/412; 204/153.22
[58] Field of Search ................. 324/425, 438, 324/439, 441, 444, 693; 204/406, 412, 431, 432, 433, 435, 153.22

[56] References Cited

U.S. PATENT DOCUMENTS

| | | | |
|---|---|---|---|
| 4,225,410 | 9/1980 | Pace | 204/195 R |
| 4,682,113 | 7/1987 | Barben | 324/441 |
| 5,103,179 | 4/1992 | Thomas et al. | 324/438 |
| 5,120,421 | 6/1992 | Glass et al. | 204/406 |
| 5,306,414 | 4/1994 | Glass et al. | 204/412 |
| 5,336,388 | 8/1994 | Leader et al. | 204/406 |
| 5,342,498 | 8/1994 | Graves et al. | 204/406 |
| 5,342,510 | 8/1994 | Eden et al. | 324/438 X |

FOREIGN PATENT DOCUMENTS

| | | |
|---|---|---|
| 0278177 | 8/1988 | European Pat. Off. |
| 2213269 | 8/1989 | United Kingdom |
| 87/05747 | 9/1987 | WIPO |
| 89/04061 | 5/1989 | WIPO |

Primary Examiner—Kenneth A. Wieder
Assistant Examiner—Glenn W. Brown
Attorney, Agent, or Firm—Keck, Mahin & Cate

[57] ABSTRACT

Water quality sensor apparatus comprising a substrate on which a plurality of sensors are supported in spaced apart relationship, each sensor being responsive to a different water characteristic and each sensor comprising a sensor region which, in use, is arranged to be contiguous with water the characteristics of which are to be sensed, which sensor regions are electrically connected to connector means via conductors supported on the substrate, the conductors and the connector means being arranged to be non-contiguous with the water in use of the apparatus.

15 Claims, 9 Drawing Sheets

24 {
- MEMBRANE + SILVER HALIDE
- SILVER HALIDE
- DIELECTRIC
- POROUS DIELECTRIC
- METAL OXIDE
- SILVER
- PLATINUM

WATER QUALITY SENSOR APPARATUS

This invention relates to water quality sensor apparatus and more especially it relates to apparatus for sensing contemporaneously a plurality of different characteristics appertaining to the quality of water.

It is known to provide, for pollution control purposes for example, water quality monitoring apparatus which comprises a submersible assembly of individually fabricated sensors, one for each characteristic to be monitored. This known apparatus has several disadvantages including high cost of manufacture, comparatively large size and inconvenient accessibility to the sensors for maintenance purposes.

It is an object of the present invention to provide an improved water quality sensor apparatus wherein one or more of the foregoing problems is substantially obviated.

According to the present invention water quality sensor apparatus comprises a substrate on which a plurality of sensors are supported in spaced apart relationship, each sensor being responsive to a different water characteristic and each sensor comprising a sensor region which, in use, is arranged to be contiguous with water the characteristics of which are to be sensed, which sensor regions are electrically connected to connector means via conductors supported on the substrate, the conductors and the connector means being arranged to be non-contiguous with the water in use of the apparatus.

In one embodiment of the invention, the substrate is flat but in alternative embodiments the substrate may be cylindrical and/or tubular, the sensors being carried on an inner or outer cylindrical surface.

Sensors may be provided for dissolved oxygen, pH conductivity, and temperature.

Reference electrodes may additionally be provided on the same substrate or alternatively they may comprise a separate assembly, and a redox sensor may also be provided.

In one embodiment of the invention, a dielectric substrate is provided having supported on one side thereof reference electrodes, a dissolved oxygen sensor and a pH sensor, and on the other side thereof in juxtaposition therewith a temperature sensor, a redox sensor and a conductivity sensor.

The sensors may be laid down on the substrate using thick film techniques.

The reference electrodes may comprise a silver halide region to which on one side thereof an electrical connection is made from one of the conductors and having on the other side thereof an insulative dielectric filled with a soluble salt of the corresponding halide, to which in use, electrical connection is made by the water.

The halide may be chloride and the salt may be potassium chloride.

The pH sensor may comprise a layer of noble metal to which electrical connection with one of the conductors is made and over which is laid an oxide of antimony, ruthenium or iridium or other suitable metal to which in use electrical connection is made by the water.

The noble metal may be platinum.

The oxide may comprise a surface region of a metal which corresponds to the oxide or an oxide filler supported in a dielectric material.

The conductivity sensor may comprise a plurality of conductors, between which the water in use is introduced.

The temperature sensor may comprise a conductive stripe carried on the substrate, the temperature of the water being measured in dependence upon the resistance of the stripe.

One embodiment of the invention will now be described by way of example only with reference to the accompanying drawings, in which;

FIG. 3b is a plan view of the other side of the sensor array shown in FIG. 3a;

Figure 1:
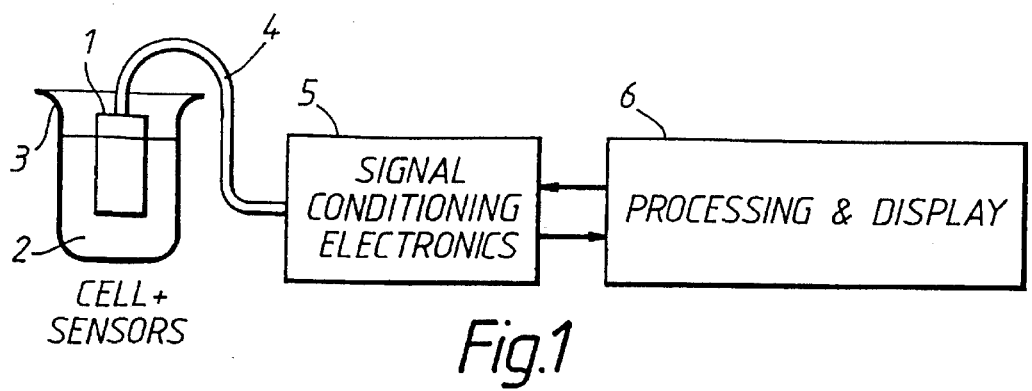
FIG. 1 is a schematic block diagram of a water quality sensor system.

Referring now to FIG. 1, a sensor system for water quality monitoring comprises a sensor array 1 which is immersed in water 2, the quality of which is to be monitored, the water being contained in a beaker 3. Signals from the sensor array are fed via electrical conductors 4 to signal conditioning electronics 5. Signals derived via the signal conditioning electronics are fed to a processor and display unit 6.

Figure 2:
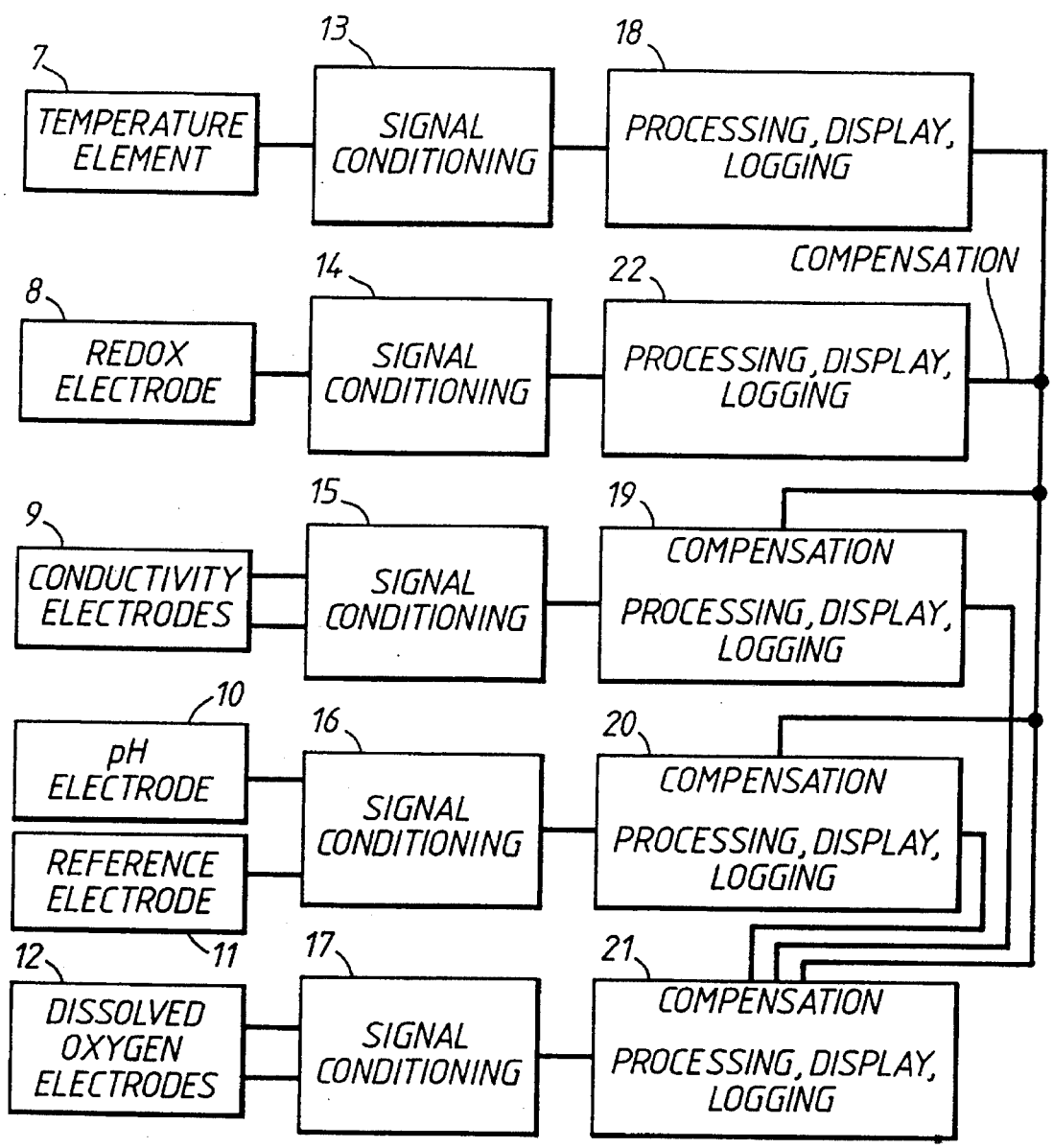
FIG. 2 is a generally schematic block diagram of a part of the system shown in FIG. 1.

Referring now to FIG. 2, the sensor array 1 comprises a temperature sensor 7, a redox sensor electrode 8, conductivity sensor electrodes 9, a pH sensor electrode 10, a reference electrode 11 and dissolved oxygen sensor electrodes 12. Signals from the sensors 7 to 12 are fed to signal conditioning circuits 13 to 17 as shown in the drawing, which in turn are connected as shown in the drawing, to processor display and data logging units 18 to 22.

Figure 3A:
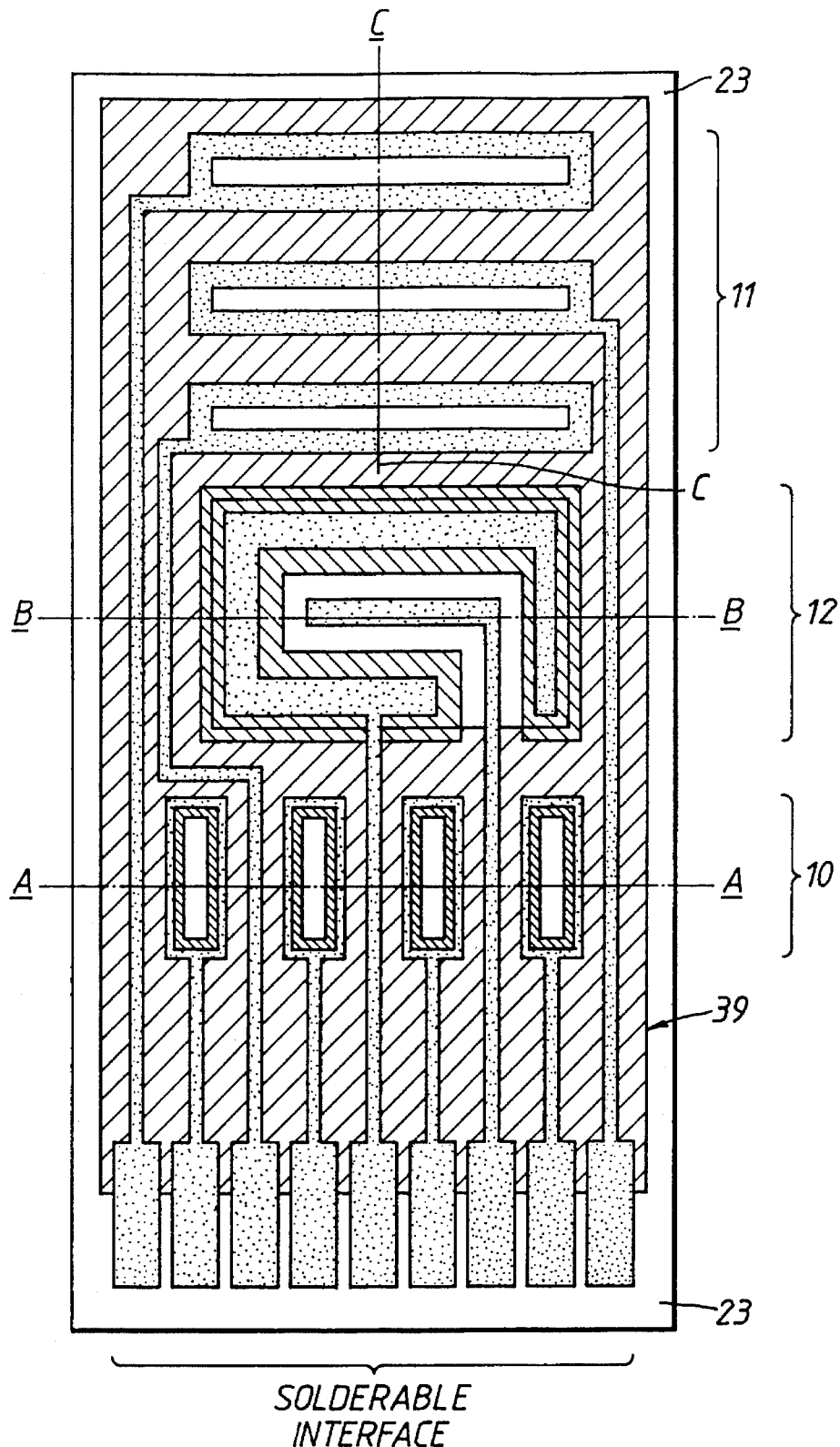
FIG. 3a is a plan view of one side of a sensor array.
Figure 3B:
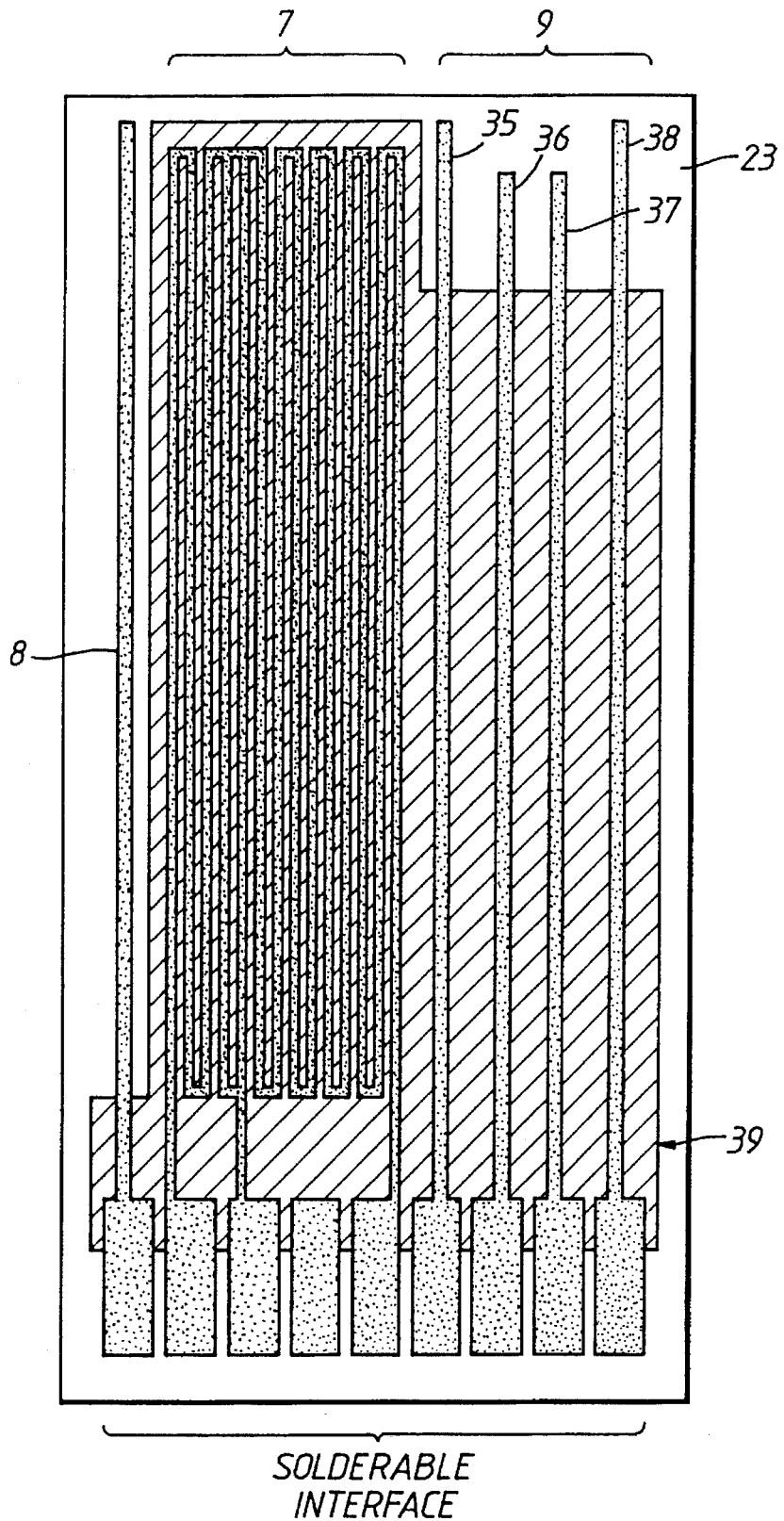
Figure 3C:
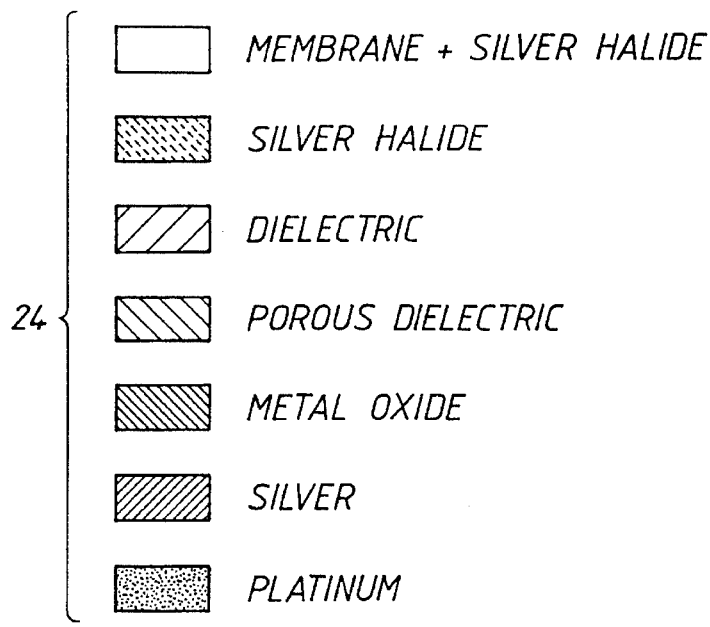
FIG. 3c is a sectional view on a line A as shown in FIG. 3a of the sensor array shown in FIGS. 3a and 3b.
Figure 3C:
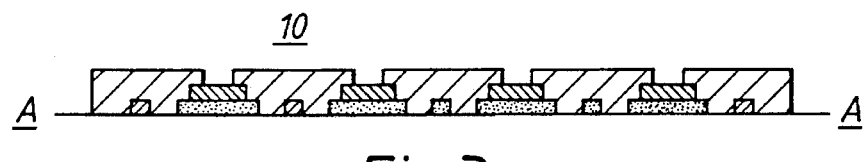
Figure 3D:
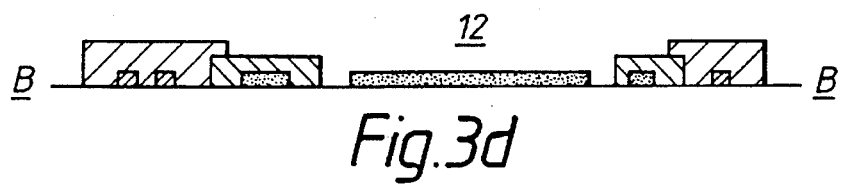
FIG. 3d is a sectional view on a line B as shown in FIG. 3a of the sensor array shown in FIGS. 3a and 3b.
Figure 3E:
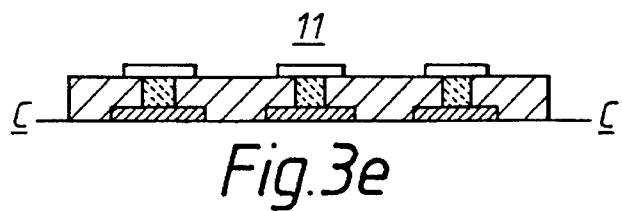
FIG. 3e is a sectional view on a line C as shown in FIG. 3a of the sensor array shown in FIGS. 3a and 3b.

Referring now to FIGS. 3a to 3d, the sensors 7 to 12 are all supported on a ceramic substrate 23, the pH sensors 10, the reference electrodes 11 and the dissolved oxygen sensor 12 being supported on one side of the substrate 23, as shown in FIG. 3a, the temperature sensor 7, the redox sensor electrode 8 and the conductivity sensor 9 being supported on the other side of the substrate 23, as shown in FIG. 3b. Sectional views through lines A, B and C are provided in FIGS. 3c, 3d and 3e, respectively to illustrate the pH sensor 10, the reference electrodes 11 and the dissolved oxygen sensor 12. Materials from which the sensors are fabricated are shown by means of a key 24 and the sensors are fabricated using the materials shown, using thick film techniques as will be apparent to those skilled in the art.

Figure 4A:
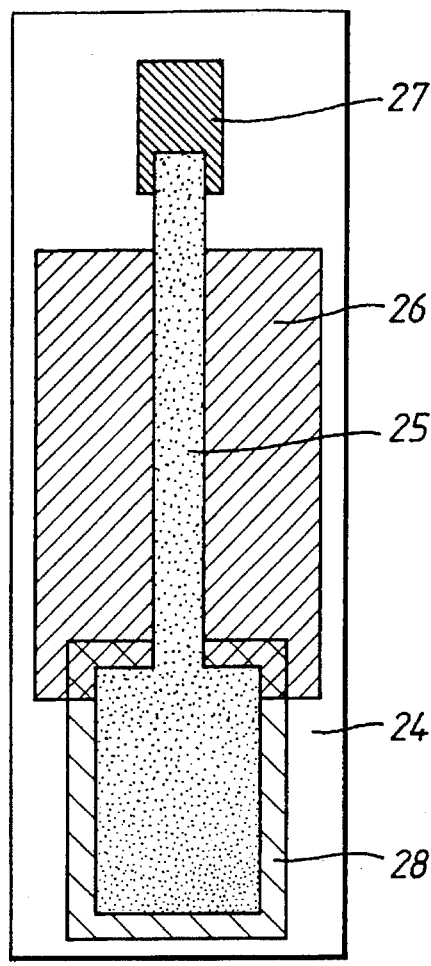
FIGS. 4a and 4b are respectively a plan view and a side view of a thick film pH sensor.
Figure 4B:
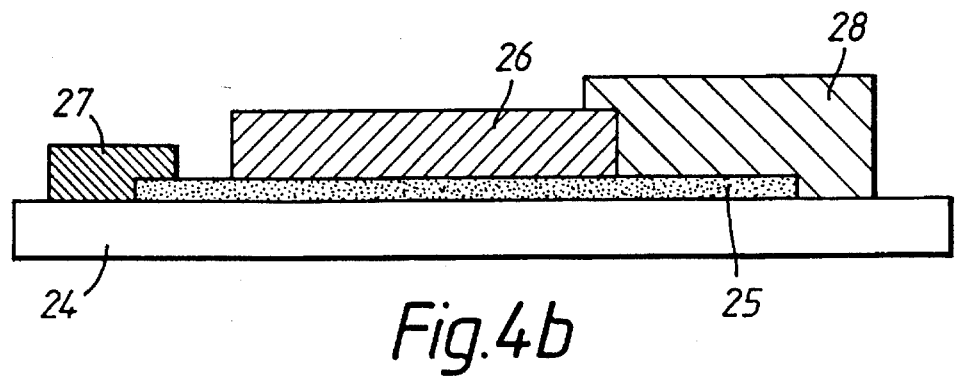

The manner in which a pH sensor corresponding to the pH sensor 10, shown in FIG. 2 and 3a, is constructed will now be considered in more detail, with reference to FIGS. 4a and 4b, wherein corresponding parts bear the same numerical designations.

Referring now to FIGS. 4a and 4b, a pH sensor comprises a substrate of ceramic material 24, on which is supported a noble metal electrode 25, which in this case is platinum. An insulation layer 26 is provided which overlays the platinum layer 25 and from which is arranged to extend a solderable electrical contact edge 27, which is electrically connected to the platinum layer 25. A pH sensitive metal oxide region 28 is provided at one end of the platinum layer 25, the oxide comprising an oxide of antimony, ruthenium, or iridium or other suitable metal, which is contained in a printable medium such as a polymer dielectric paste.

Figure 5A:
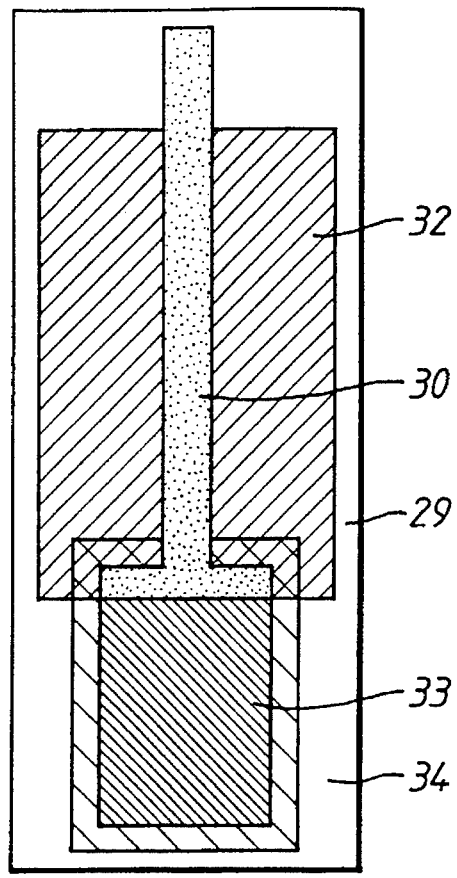
FIGS. 5a and 5b are respectively a plan view and a side view of a thick film reference electrode.
Figure 5B:
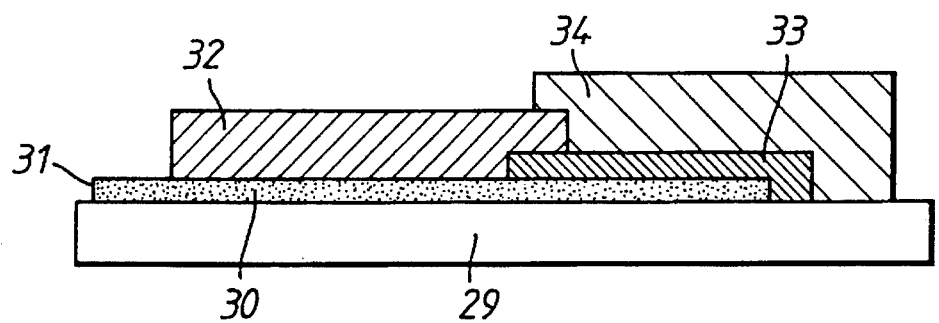

Referring now to FIG. 5a and 5b, a reference electrode arrangement is shown wherein corresponding parts of the two figures bear the same numerical designations. The reference electrode shown corresponds to the reference electrodes 11, shown in FIGS. 2 and 3a, and comprises a substrate of ceramic material 29 which is arranged to carry a silver electrode 30, which provides a solderable interface region 31 to which electrical connection can be made. Overlaying the silver electrode 30, an insulation layer 32 is provided and at the end thereof remote the connection interface 31, a silver halide region 33 is formed which may, for example comprise silver chloride. Overlaying the silver halide region 33, a halide salt region 34, comprising for example potassium chloride, is provided in the form a printable medium, comprising a polymer paste.

In the case of the pH sensor, as shown in FIGS. 4a and 4b the metal oxide region 28 is exposed to the water for pH sensing purposes and in the case of the reference electrode, as shown in FIGS. 5a and 5b, the halide salt region 34 is exposed to the water under test for sensing purposes.

Figure 6:
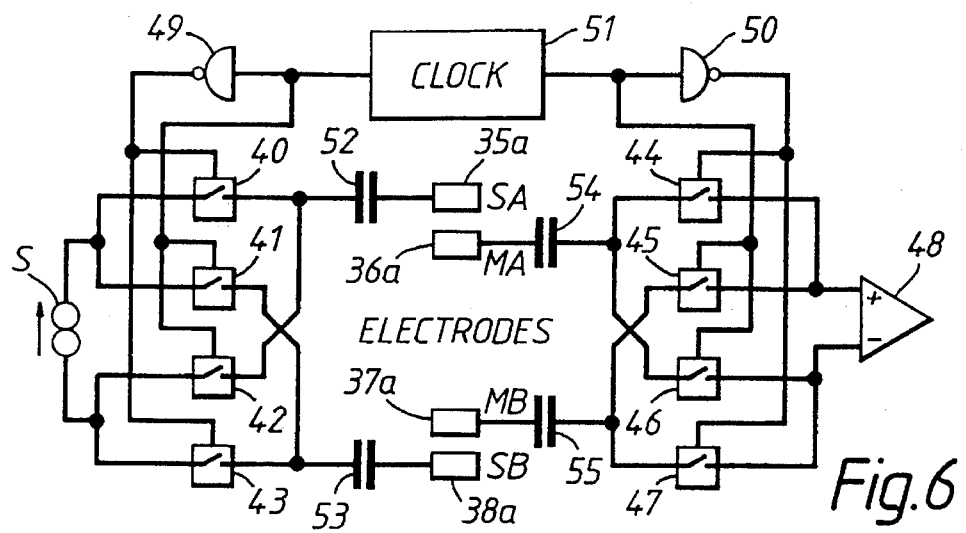
FIG. 6 is a circuit diagram suitable for four terminal conductivity measurement.

As shown in FIG. 3b, conductivity measuring electrodes 35, 36, 37 and 38 are provided which facilitate a four terminal conductivity measurement. For the purpose of this measurement, outer electrodes 35 and 38 are used as source electrodes to pass a current through the water under test and inner electrodes 36 and 37 are used as sense electrodes responsive to a potential difference. As shown in FIG. 3b, end portions only of the electrodes 35 to 38 are exposed to the water under test, the remainder of the electrodes being insulated by means of a passivation layer 39 which serves to protect them from the water. A circuit used for four terminal conductivity measurement is shown in FIGS. 6, wherein connections from electrodes 35 to 38 are made to corresponding input terminals 35a to 38a.

The measurement method involves the use of electronic switches 40 to 43 which serve to convert a dc current from a source S into an ac square wave and a further set of switches 44 to 47 which serve to convert the square wave measured in the liquid back into a dc voltage which is applied to a differential amplifier 48. Capacitors 52 to 55 are provided for coupling purposes and serve an additional function as hereinafter described.

Figure 7A:
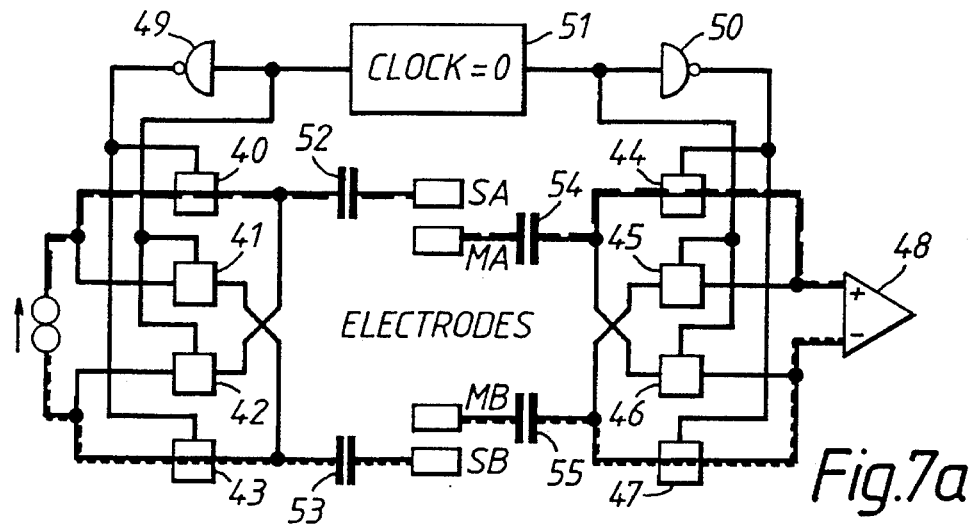
FIGS. 7a and 7b are circuit diagrams appertaining respectively to clock low and clock high conditions of the circuit shown in FIG. 6.
Figure 7B:
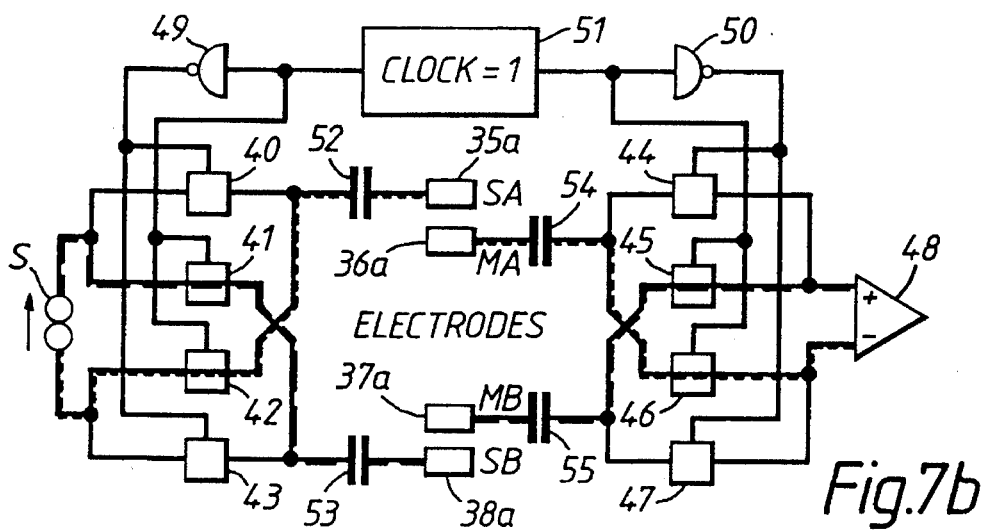

The manner of operation of the circuit to produce the specified result will be readily apparent to those skilled in the art, and accordingly further description of the mode of operation is believed to be unnecessary. As shown in FIGS. 2, 7a and 7b however, the paths of the currents and potentials during each half cycle are illustrated by means of thick and thin broken lines respectively and it can be seen that the water under test experiences an ac signal with no dc component whilst the current source in the differential amplifier experiences a continuous dc current whereby low cost accurate dc electronics can be used to make an ac measurement.

Figure 8A:
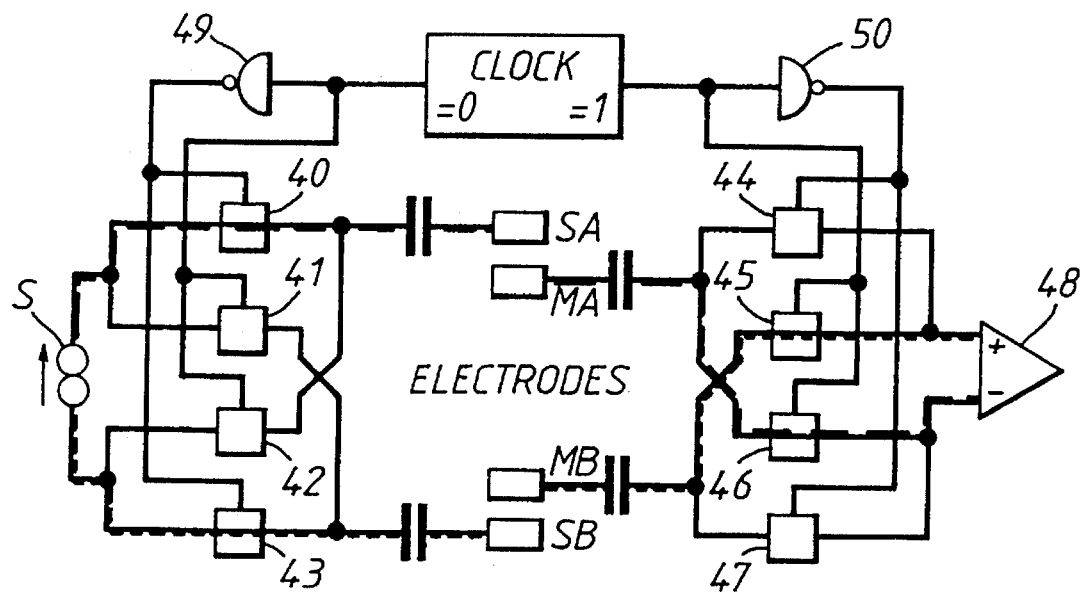
FIGS. 8a and 8b are respectively circuit diagrams appertaining to reversed plurality modes appertaining to operation of the circuit shown in FIG. 6.
Figure 8B:
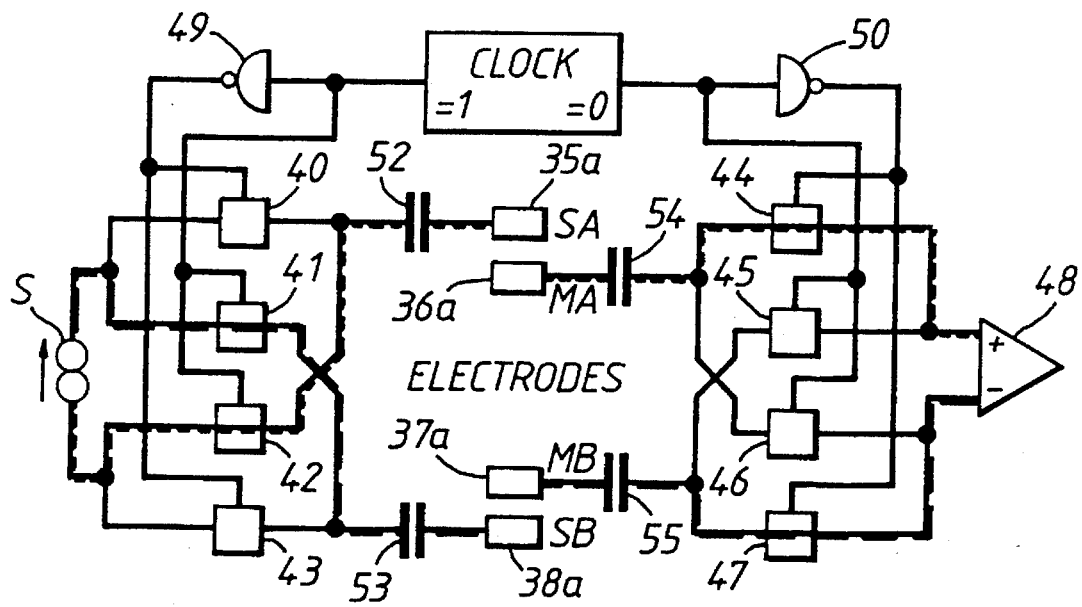

As shown in FIG. 8a and FIG. 8b, the relative phase of the clock pulse signals to the source and measurement electronic switches can be reversed. This has the effect of reversing the polarity of the signal as sensed at the differential amplifier, as illustrated in FIG. 8a and FIG. 8b. Thus by doing two measurements with the clock pulse signals alternately in-phase and out of phase and by taking the difference between the differential amplifier outputs for each measurement, effects produced due to offset voltages in the amplifier and measurement system, are effectively cancelled whereby they are eliminated so that high accuracy is afforded, which is especially important when measuring small potential differences.

The circuit thus far described, lends itself to refinements which will now be considered. Firstly, switching signals to the source switches 40 to 43 are overlapped to give a 'make before break' action. This ensures that the current source or sources are not allowed to saturate during switching and additionally ensures that the capacitors 52 to 55 are allowed to discharge fully in case the current source and solution are isolated from each other.

Secondly, the 'on' period of the switching signals to the measuring electrodes switches 44 to 47 are effectively shortened so that all switches are in an 'off' condition whilst the source switches are being switched. This ensures that any transient effects caused by the switching, or non-linear transient effects in the solution do not appear at the inputs to the differential amplifier 48. The capacitors serve in effect to hold the potential at the amplifier inputs during the 'off' periods.

Figure 9:
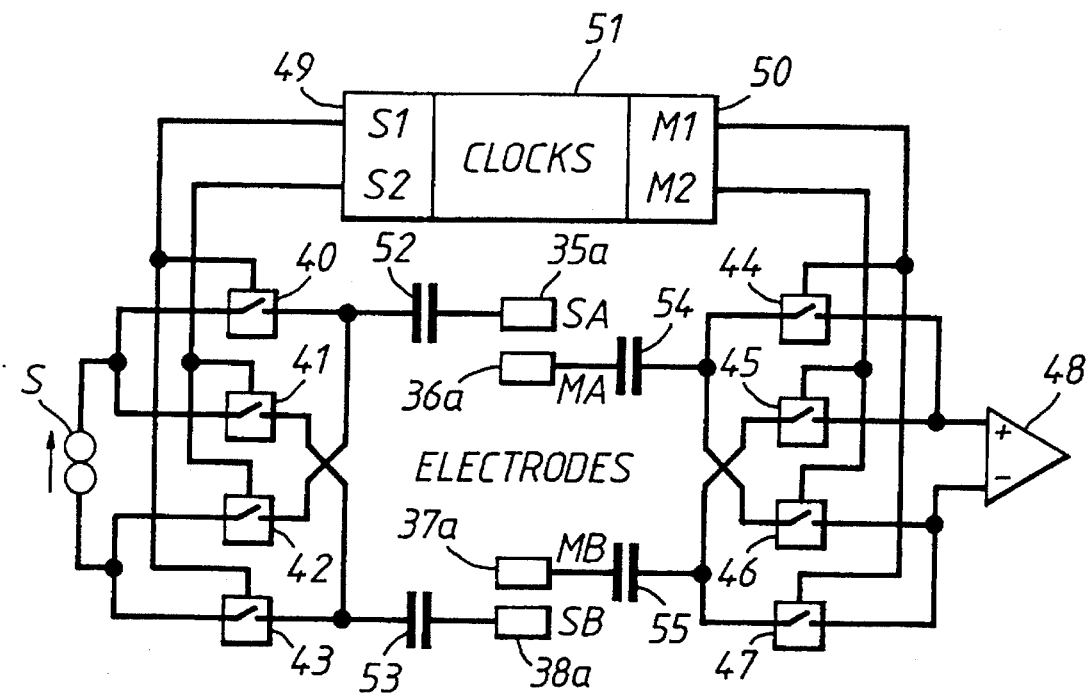
FIG. 9 is a circuit diagram which is a modification of the circuit shown in FIG. 6, comprising separated switching signals.
Figure 10:
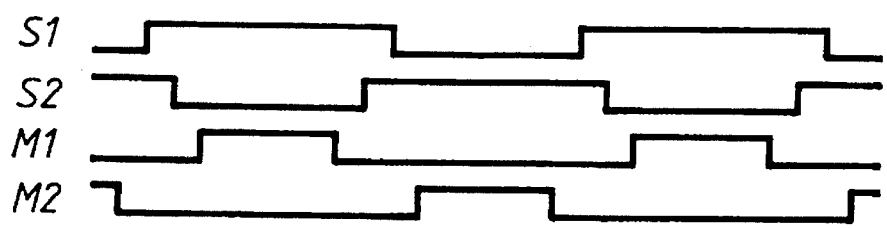
FIG. 10 is a wave form diagram appertaining to the circuit shown in FIG. 9.

Referring now to FIG. 9, the circuit shown corresponds substantially with that shown in FIG. 6, but the clock connections have been re-drawn and numbered S1, S2, M1 and M2 which correspond with switching wave forms bearing the same designations as shown in FIG. 10. The main advantages afforded by the four terminal conductivity measurement as just before described, stems from the use of switches to facilitate the provision of ac current from a dc source and the embodiment of circuitry which facilitates phase reversal to eliminate 'off set' effects.

In order to facilitate redox measurement, electrode 8 is provided which may simply comprise an electrode of noble metal such as platinum.

In order to facilitate temperature measurement, the temperature sensor 11 comprises a conductive stripe which is tapped to define a potentiometer, the conductive parts of the stripe being insulated from the water and from each other by the passivation layer 39.

By providing in a system as shown generally in FIG. 1, having a sensor array as hereinbefore described, the provision of apparatus is afforded which is inexpensive to fabricate, convenient to use and easy to maintain.

We claim:

1. Water quality sensor apparatus comprising a substrate on which a plurality of sensors are supported in spaced apart relationship, each sensor being responsive to a different water characteristic and each sensor comprising a sensor region which, in use, is arranged to be contiguous with water the characteristics of which are to be sensed, which sensor regions are electrically connected to connector means via conductors supported on the substrate, the conductors and the connector means being arranged non-contiguously with the water in use of the apparatus.

2. Apparatus as claimed in claim 1, wherein the substrate is flat.

3. Apparatus as claimed in claim 1, wherein the substrate is cylindrical and/or tubular, the sensors being carried on an inner or outer cylindrical surface.

4. Apparatus as claimed in claim 1, wherein the sensors are provided for dissolved oxygen, pH, conductivity, and temperature.

5. Apparatus as claimed in claim 4, wherein reference sensor electrodes are additionally provided on the substrate together with a redox sensor electrode.

6. Apparatus as claimed in claim 1, wherein the substrate comprises a dielectric having supported on one side thereof reference sensor electrodes, a dissolved oxygen sensor and a pH sensor, and on the other side thereof in juxtaposition therewith a temperature sensor, a redox sensor and a conductivity sensor.

7. Apparatus as claimed in claim 1, wherein the sensors are laid down on the substrate using thick film techniques.

8. Apparatus as claimed in claim 5, wherein the reference electrode(s) comprises a silver halide region to which on one side thereof an electrical connection is made from one of the conductors and having on the other side thereof an insulative dielectric filled with a soluble salt of the corresponding halide, to which in use, electrical connection is made by the water.

9. Apparatus as claimed in claim 8, wherein the halide is chloride and the salt is potassium chloride.

10. Apparatus as claimed in claim 4, wherein the pH sensor comprises a layer of noble metal to which electrical connection with one of the conductors is made and over which is laid an oxide of antimony, ruthenium or iridium or other suitable metal to which in use electrical connection is made by the water.

11. Apparatus as claimed in claim 10, wherein the noble metal is platinum.

12. Apparatus as claimed in claim 10, wherein the oxide comprises a surface region of a metal which corresponds to the oxide or an oxide filler supported in a dielectric material.

13. Apparatus as claimed in claim 4, wherein the conductivity sensor comprises a plurality of conductors, between which the water in use is introduced and which serve to facilitate four terminal measurement.

14. Apparatus as claimed in claim 13, wherein two source electrodes and two measurement electrodes are provided for said four terminal measurement, the source electrodes being fed with ac current from a dc source via a switching inverter and the measurement electrodes being coupled to a differential amplifier via a switching circuit which serves to convert an ac signal measured to a dc signal which is applied across the differential amplifier.

15. Apparatus as claimed in 4, wherein the temperature sensor comprises a conductive stripe carried on the substrate, the temperature of the water being measured in dependence upon the resistance of the stripe.

* * * * *